United States Patent [19]

Finger

[11] Patent Number: Plant 5,889

[45] Date of Patent: Feb. 24, 1987

[54] KALANCHOE PLANT NAMED FASCINATION

[75] Inventor: Hermann Finger, Wiesmoor, Fed. Rep. of Germany

[73] Assignee: Wiesmoor-Gartnerie und Baumschule GmbH, Fed. Rep. of Germany

[21] Appl. No.: 750,600

[22] Filed: Jul. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct Kalanchoe plant named Fascination, having an abundance of lavender pink flowers, excellent branching; small, relatively dark and dense foliage, compact growth habit, early flowering and good keeping qualities.

1 Drawing Figure

The present invention relates to a new and distinctive cultivar of Kalanchoe plant, botanically known as *Kalanchoe blossfeldiana*, and referred to by the cultivar name Fascination.

Fascination was developed by me through controlled breeding by crossing Ceylon (seed parent) with Bali (pollen parent). Asexual reproduction of stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry:

1. Fascination is characterized by its abundance of flowers, excellent basal and side branching, and early flowering.

2. Branching in Fascination is better than the branching of the cultivars Bali (disclosed in U.S. Plant Pat. No. 5,348), Acapulco (disclosed in U.S. Plant Pat. No. 5,384) and Satisfaction, and is equal to the cultivar Attraction. Satisfaction and Attraction are cultivars of Applicant disclosed in pending applications.

3. The plant growth rate of Fascination is similar to Attraction and Satisfaction, and faster than Acapulco.

4. Foliage is small and dense, being crenate like Satisfaction and Acapulco. Bali and Attraction have dentate foliage.

5. Growth rate, high degree of self branching, and flowering make the cultivar suitable for 10 cm pot production.

6. After flower initiation plants must be treated with Alar in all seasons to reduce peduncle elongation.

7. Flowering time is 9 weeks in summer to 12 weeks in winter after start of short days. This is earlier than Bali which is 10 weeks in summer and similar to Satisfaction, Attraction and Acapulco.

8. The flower color is lavender pink and very similar to Acapulco, and deeper than Satisfaction. Fascination has many more flowers than Acapulco.

9. Flower petals are pointed at the tip, and flower size is generally similar to the cultivars referred to, except for Bali which is slightly smaller in size.

10. Its dark leaves are rounded, similar to Satisfaction and Acapulco. Leaves are similar to Bali in thickness but not as thick as Acapulco.

The accompanying colored photograph illustrates the overall appearance of Fascination taken as a perspective view of the plant, and showing the colors as true as it is reasonably possible to obtain in a colored reproduction of this type.

The following is a detailed description of Fascination based on plants produced under commercial practices in the greenhouses of Wiesmoor Gartnerei in Wiesmoor, Germany. Color references are made to The Royal Horticultural Society Colour Chart except where general terms of ordinary dictionary significance are used.

Parentage: A controlled cross between Ceylon and Bali.

Propagation:

(A) *Type cutting.*—Short stem cutting up to 2 cm long.

(B) *Time to root.*—10 days at 21° C. summer. 14 days at 21° C. winter.

(C) *Rooting habit.*—Many fine fibrous roots.

Plant description:

(A) *Form.*—Short, compact, best suited for growing and scheduling practices in 10 cm pots.

(B) *Habit of growth.*—Moderate rate of growth with shoots formed generally at every node.

(C) *Foliage description.*—Leaves simple, opposite. (1) Size: Mature leaf on a plant grown in a 10 cm pot is typically 110 mm long and 60 mm wide. (2) Shape: Obovate with obtuse apex and rounded base. (3) Texture: Glabrous, coriaceous, succulent. (4) Margin: Crenate. (5) Color: Young foliage, top side 146A; under side 146C; Mature foliage, top side 147A; under side 146A.

Flowering description (A) *Flowering habits.*—Cyme inflorescence; each shoot is formed by dichotomous branching, starting with the opening of the terminal flower of the main axis, followed by terminal flowers of the side branching, continuing with subsequent development of branches in the inflorescence. Major inflorescence is 50 mm to 60 mm in diameter and lateral inflorescences are 30 mm to 40 mm in diameter.

(B) *Natural flowering season.*—Early January. Flowering time under controlled day length at 20° C. in summer is 9 weeks; in winter is 12 weeks. Flowering time depends on temperature, light intensity, and other growing conditions.

(C) *Flower buds.*—Oblong up to 9 mm long, developing to tubular as flower petals mature, sheathed with four light green sepals; corolla at maturity is 8 mm long.

(D) *Flowers borne.*—On compound dichasial cymes; primary peduncle is 3 mm to 4 mm in diameter, with peduncle length depending on growing conditions and Alar application; pedicels up to 7 mm long.

(E) *Quantity of flowers.*—Highly floriferous, main axis has over 100 flowers and lateral branches have over 75 flowers, with eight or more side branches.

(F) *Petals.*—(1) Shape: Generally oblong with tips pointed. (2) Color: Top when opening, 67B, fading to 67C; under side 68B–68C. (3) Number and Size of Petals: Four, united in corolla; petals 6 mm in diameter; flower 15 mm in diameter.

(G) *Reproductive organs.*—(1) Stamens: Eight in number. (a) Anther shape: Flat, elliptical; yellow in color. (b) Filament color: Light green. (c) Pollen color: Yellow. (2) Pistels: (a) Stigma: Flat shape, greenish white immature to white mature. (b) Style color: Light green. (c) Ovaries: Four-celled, 5 mm, green in color.

Disease resistance: Highly resistant to mildew. No other disease problems to date.

I claim:

1. A new and distinct cultivar of Kalanchoe named Fascination, as described and illustrated, and particularly characterized by its abundance of lavender pink flowers, excellent branching; small, relatively dark and dense foliage, compact growth habit, early flowering, and by its good keeping qualities.

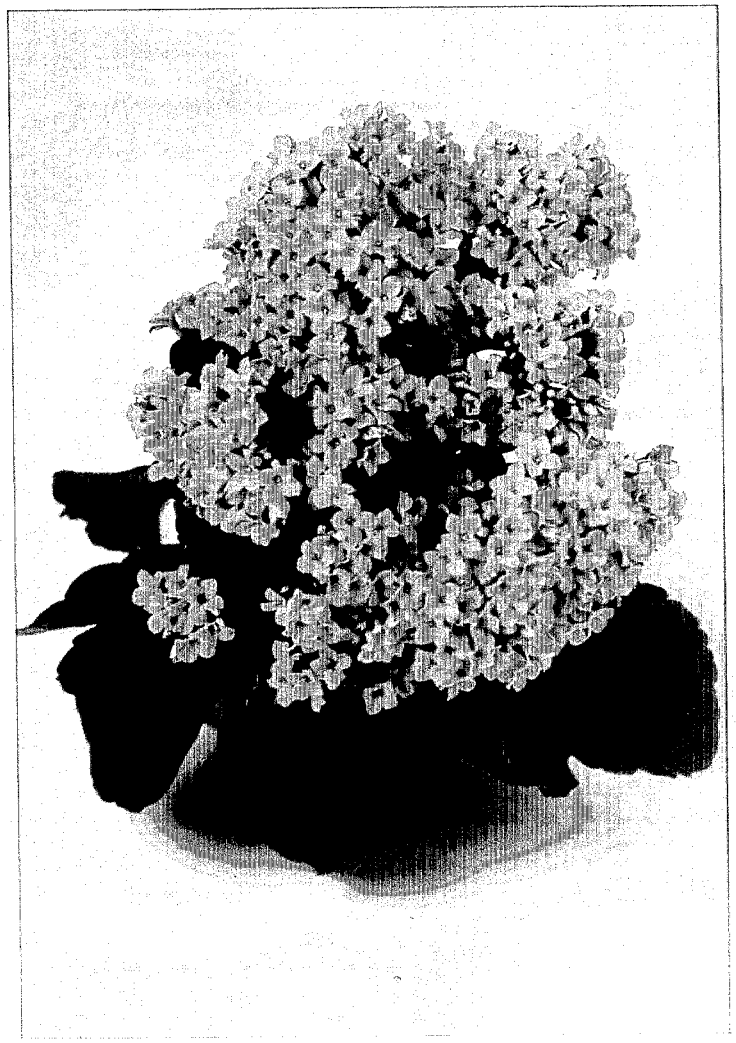

* * * * *